United States Patent [19]

Huber et al.

[11] 4,009,267

[45] Feb. 22, 1977

[54] CROSS-LINKED ORGOTEIN

[75] Inventors: Wolfgang Huber, Atherton; Mark G. Saifer, Berkeley; Lewis D. Williams, Menlo Park, all of Calif.

[73] Assignee: Diagnostic Data, Inc., Mountain View, Calif.

[22] Filed: Sept. 9, 1975

[21] Appl. No.: 611,658

[52] U.S. Cl. .......................... 424/177; 260/112 R; 260/112 B; 260/113; 260/121; 424/88; 424/287
[51] Int. Cl.[2] ................. A61K 37/02; A61K 37/14; C07G 7/04
[58] Field of Search ........... 260/112 R, 112 B, 113, 260/121, 11 R, 11 B; 424/177, 287

[56] References Cited

UNITED STATES PATENTS

| 3,687,927 | 8/1972 | Huber | 260/113 |
|---|---|---|---|
| 3,758,682 | 9/1973 | Huber | 424/177 |
| 3,813,289 | 5/1974 | Huber | 260/113 X |

OTHER PUBLICATIONS

Lenard, Chem. Abs. vol. 68, 1968 No. 92962v.
Niehaus, Chem. Abs. vol. 72, 1970, No. 108777j.

Primary Examiner—Albert T. Meyers
Assistant Examiner—A. P. Fagelson
Attorney, Agent, or Firm—Millen & White

[57] ABSTRACT

Orgotein cross-linked with itself or with non-antigenic injectable serum or tissue protein has a substantially longer half-life in the blood after injection than orgotein.

12 Claims, No Drawings

CROSS-LINKED ORGOTEIN

BACKGROUND OF THE INVENTION

This invention relates to orgotein derivatives.

Orgotein is the non-proprietary name assigned by the United States Adopted Name Council to members of a family of water-soluble protein congeners in substantially pure, injectable form, i.e., substantially free from other proteins which are admixed or associated therewith in the sources thereof. U.S. Pat. No. 3,758,682 claims pharmaceutical compositions orgotein. Various uses of orgotein are claimed in U.S. Pat. No. 3,637,441; 3,773,928; 3,773,929; and 3,781,414.

The orgotein metalloproteins are members of a family of protein congeners having a characteristic combination of physical, chemical, biological and pharmacodynamic properties. Each of these congeners is characterized physically by being the isolated, substantially pure form of a globular, buffer and water-soluble protein having a highly compact native conformation which, although heat labile, is stable to heating for several minutes at 65° C. at pH 4–10. Chemically, each is characterized by containing all but 0–2 of the protein aminoacids, a small percentage of carbohydrate, no lipids, 0.1 to 1.0% metal content provided by one to 5 gram atoms per mole of one or more chelated divalent metals having an ionic radius of 0.60 to 1.00 A., and substantially no chelated monovalent metals or those that are cell poisons in the molecule.

In 1969, the bovine congeners of the orgotein protein was discovered to be an enzyme which has the ability to catalyze the destruction of superoxide radicals in a disproportionation into molecular oxygen and hydrogen peroxide. The name superoxide dismutase (SOD) was assigned to the protein on the basis of this enzymatic activity by McCord, J. M. and Fridovich, I., J. Biol. Chem. 244, 6049–6055 (1969).

Studies with $^{99m}Tc$ labeled orgotein established that orgotein remains only briefly in the blood after intravenous administration. For example, within 15 minutes after intravenous administration of the labeled orgotein, virtually all radioactivity was found concentrated in the kidneys. A similar although less dramatic pooling of the orgotein in the kidneys also occurs after subcutaneous injection. In clinical situations where a plurality of injections of orgotein is desirable, e.g., rheumatoid arthritis and other chronic inflammatory conditions, it is desirable to maintain the orgotein in the body fluids for as long as possible.

It has now been found that orgotein cross-linked with itself or with serum or tissue protein has a much longer, e.g. 3–10 times, serum half-life than orgotein itself.

SUMMARY OF THE INVENTION

In a composition aspect, this invention relates to soluble, injectable, cross-linked orgotein. In another composition aspect, this invention relates to soluble, injectable orgotein cross-linked to an injectable serum or tissue protein.

In another aspect, this invention relates to pharmaceutical compositions adapted for parenteral administration comprising, in admixture with a pharmaceutically acceptable carrier, a cross-linked orgotein or orgotein cross-linked to a serum or tissue protein of this invention.

In process aspects, this invention relates to processes for the production of the novel compositions of this invention and to methods for their use.

DETAILED DISCUSSION

It was surprising a discover that the greatly increased molecular weight resulting from the cross-linking did not adversely affect the pharmacodynamic activity, including anti-inflammatory activity, of the orgotein.

The term "cross-linked" as used herein means an orgotein molecule is joined to at least one other orgotein molecule or to at least one injectable serum or tissue protein molecule by one or more bridging groups. The exact number of bridging groups is not critical, so long as water solubility is retained. Preferably, the orgotein is cross-linked by an average of 1–5 bridging groups, more preferably 1.

The exact chemical nature of the bridging group is not critical and can be non-functional but ordinarily contains one or more residues of the functional groups present in the cross-linking agent, e.g., carbonyl. Preferably, the bridging group is straight chain and has a molecular weight of less than about 200. Especially preferred are bridging groups which are hydrocarbon, except for two residues at the α and ω-positions thereof of the two functional groups of the cross-linking agent which reacted with the protein to achieve cross-linking.

A wide variety of cross-linking agents are suitable for cross-linking orgotein to itself or to serum albumin. For a discussion thereof, see e.g., Finn Wold in C. H. D. Hirs (Editor), "Methods in Enzymology," Vol. XI, pp. 617–640 (1967); and G. E. Means, R. E. Feeney, "Chemical Modification of Proteins," pp. 39–42 (1971), whose disclosures are incorporated by reference.

Examples of suitable cross-linking agents are: diisocyanates:

diisocyanates:
$O=C=N-(CH_2)_n-N=C=O$        n=1 through 8

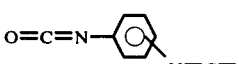

ortho, meta, para n–1–4 diisothiocyanates:
(corresponding to the above)

diimidoesters:

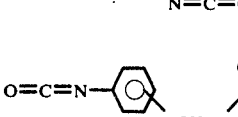

R=Me,Et  n=1–8 bis(p-nitrophenyl)diacid diesters:

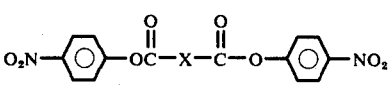

$X=(CH_2)_n$, n=1–6, X= —⟨○⟩— dialdehydes : $HOC-(CH_2)_n-COH$ wherein n = 1 to 6, especially glutaraldehyde.

Others are 1,5-difluoro-2,4-dinitrobenzene, p,p'-difluorom,m'-dinitrodiphenylsulfone, dimethyl adipimidate, phenol-2,4-disulfonyl chloride; formaldehyde, Woodward's reagent K and bisdiazobenzodine.

Any injectable serum or tissue protein which is non-antigenic and injectable can be employed to produce orgotein cross-linked with protein. Because antigenicity is in part dependent upon the species of animal from which the protein is obtained, i.e., protein obtained from a species different than the recipient patient can be antigenic to varying degrees, and because humans are a preferred class of patients for orgotein therapy, the preferred proteins are human proteins. However, proteins from other species of mammal, e.g., horse, cow, dog, cat, etc., are useful for producing orgotein-protein cross-linked products especially suitable for therapy in these animals, respectively. Although protein from the same species as the intended patient is preferred as starting material, it is not vital that the same species of proteins be employed, as an antigenic response is usually within tolerable limits.

Preferred classes of injectable proteins are injectable soluble globulin and albumin proteins. Of these, serum albumin is especially preferred.

An example of human albumin suitable as starting materials for the orgotein-albumin cross-linking aspect of the process of this invention are stable human blood plasma protein fractions. Stable plasma protein fractions are those which survive at up to 60° C. for up to 10 hours and typically consist predominantly of albumin plus small amounts of alpha and beta globulins.

A preferred class of such starting materials is a non-homogeneous plasma protein fraction, e.g., that obtained from Supernatant IV-1 by precipitation with ethanol (Cohn Method 6 process), which protein fraction has been reconstituted to a 5% solution (containing NaCl and a stabilizer, e.g., acetyl tryptophan and/or sodium caprylate) and then heated to 60° C. for 10 hours to destroy hepatitis virus. This stable plasma protein fraction is described in Japanese Pat. No. 265,704 and U.S. Pat. No. 2,958,628. Another group of starting materials are solutions of plasma protein fractions which have been heated at about 60° C. for shorter periods of time, e.g., between about 2 to 10 hours, can also be used.

Another suitable starting material is the soluble albumin obtained by extraction of human placenta with 15 saline solution and preferably therafter heat treated as described above. For a further description of such starting materials, see U.S. Pat. No. 3,876,775.

Because the likelihood of antigenic effects increases with increasing molecular weight, the cross-linked orgoteins preferably have a molecular weight of up to 500,000, more preferably up to 200,000, most preferably up to 100,000. When two orgotein molecules are cross-linked together, the molecular weight of the cross-linked product is approximately 65,000. When three orgotein molecules or one orgotein and one serum albumin molecule are cross-linked together the molecular weight of the cross-linked product is about 98,000. When two molecules of orgotein are cross-linked with a single molecule of serum albumin, the molecular weight is about 131,000 In each case, the exact value depends on the molecular weights of the albumin and of the residue of the cross-linking agent forming the cross-linking bridge.

The molecular ratio of orgotein to other injectable serum or tissue protein can be determined by determining the approximate molecular weight by gel chromatography or other known method for determining the molecular weight of proteins and by determining its chelated copper and/or zinc content, since orgotein is unique among proteins in containing both of these metals.

The pharmaceutical compositions of this invention comprise a cross-linked orgotein of this invention and a pharmaceutically acceptable carrier. The form and character which this carrier takes is, of course, dictated by the mode of administration.

The pharmaceutical composition preferably is in the form of a sterile injectable preparation, for example, as a sterile injectable aqueous solution. The solution can be formulated according to the known art using those carriers mentioned above. The sterile injectable preparation can also be a sterile injectable solution or suspension in a non-toxic parenternally acceptable diluent or solvent, e.g., 1,3-butanediol.

The compositions of this invention combine an effective unit dosage amount of a cross-linked orgotein of this invention, e.g., the cross-linked orgotein is present at a concentration effective to evoke the desired response when a unit dose of the composition is administered by the route appropriate for the particular pharmaceutical carrier. For example, liquid compositions, both topical and injectable, usually contain about 0.5 to 20 mg. of cross-linked orgotein per 0.25 to 10 cc., preferably about 0.5 to 5 cc., except I.V. infusion solutions, which can also be more dilute, e.g., 0.5 to 20 mg. of cross-linked orgotein per 50–1,000 ml., preferably 100–500 ml of infusion solution. Tablets, capsules and suppositories usually contain 0.1 to 25 mg., preferably 1 to 10 mg., of cross-linked orgotein per unit.

Cross-linked orgotein usually is administered by instillation or by injection, e.g., intramuscularly, subcutaneously, intravenously or intradermally. I.M. is preferred, except in case of shock where I.V. is sometimes preferred for more rapid onset of effect, and in certain localized disorders, e.g., radiation and other cystitis, where local injection, instillation and/or infusion, is often more effective. Individual doses usually fall within the range of 0.5 to 20 mg. The preferred range for humans is about 0.5 to 8 mg.: for horses, about 5.0–10.0 mg. The exact dosage is not critical and depends on the type and severiety of the disease.

Cross-linked orgotein, like orgotein, is effective in treating a wide variety of inflammatory conditions, including those in which synthetic anti-inflammatory agents have limited utility, e.g., because of toxic side effects upon prolonged use.

More specifically cross-linked orgotein is efficacious in ameliorating inflammatory conditions and mitigating the effects thereof, for instance those involving the urinary tract and the joints, in various mammals. It is useful in alleviating the symptoms of and the structural deformities associated with post-traumatic arthritis, and rheumatoid diseases, such as bursitis, tendonitis, osteoarthritis.

For further details relating to how to isolate the starting orgotein congeners and how to use the cross-linked orgotein of this invention, including modes of administration, dosage forms, dosage regimen and inflammatory and other conditions susceptible to treatment with cross-linked orgotein, see U.S. Pat. No. 3,758,682, whose disclosure is incorporated by reference.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever.

EXAMPLE 1

Bovine Orgotein Cross-linked by Glutaraldehyde

The reaction of 0.34 mg. of bovine orgotein (1.7 mg/ml) with 0.2 mg. glutaraldehyde (0.1%) in 0.2 ml. of 0.01 M NaCl plus 0.01 M pH 7.5 phosphate buffer solution is complete within 15 minutes at room temperature to give a mixture of electrophoretically more anodic (bands 1–6) Superoxide Dismutase (SOD) species. The product is a mixture of unchanged orgotein and orgotein cross-linked through amino groups to one or two other orgotein molecules and having molecular volumes corresponding to a molecular weight from about 30,000 (unchanged orgotein) to about 100,000. The orgotein and cross-linked orgotein dimer and trimer are separated by gel chromatography (Sephadex G-200 or BioGel A 0.5).

Following the procedure of Example 1, employing the corresponding human, sheep, horse, pig, dog, rabbit, guinea pig and chicken orgotein congeners as starting protein, crosslinked products of these congeners are produced in which 2 or 3 orgotein molecules are joined together by bridging glutaraldehyde residues. These dimeric and trimeric crosslinked products are readily separated by gel chromatography employing Sephadex G-200.

EXAMPLE 2

Bovine Orgotein Cross-linked to Bovine Serum Albumin by Glutaraldehyde

Following the procedure of Example 1, bovine orgotein is cross-linked to crystalline bovine serum albumin (Miles Laboratories, Pentex Div.) by the reaction of a mixture of 1 mg. of orgotein (1.7 mg/ml), 2 mg. of bovine serum albumin (BSA, 3.3 mg/ml) and 0.6 mg. of glutaraldehyde (0.1%) in 0.6 ml. of 0.01 M NaCl 0.01 M pH 7.5 phosphate buffer solution. Electrophoresis of the reaction mixture shows the same more anodic (SOD) active bands as in Example 1, viz., orgotein cross-linked with itself, plus a SOD active band electrophoresing with BSA, viz., orgotein cross-linked to the bovine serum albumin.

Gel chromatography (Bio-Gel A 0.5) indicates that the SOD active species electrophoresing with BSA has a molecular volume between that of BSA and that of catalase (M.W. 100,000 – 200,000), and are orgotein cross-linked with one molecule of BSA and orgotein cross-linked with two molecules of BSA, respectively, and that the glutaraldehyde-orgotein bands more anodic than orgotein have a molecular volume up to several times that of native orgotein and correspond to the cross-linked orgoteins obtained in Example 1. The various cross-linked species are separated by gel chromatography as described above.

Glutaraldehyde concentrations above 0.5% give more heterogeneous protein species and lower overall SOD activity, probably resulting from higher polymerization and/or intramolecular reactions.

Following the above procedure of Example 2 but substituting human, sheep, pig, dog, rabbit, guinea pig, and chicken serum albumin, respectivly, e.g., the heat stable human serum albumin described above, for the BSA there is obtained, the bovine orgotein congener cross-linked to the selected serum albumin. Similarly, human, bovine or other orgotein congener is cross-linked with human globulin, e.g., gammaglobulin.

EXAMPLE 3

Orgotein Cross-linked by Bis-Diazobenzodine

Diazonium salts react with tyrosine, histidine and lysine residues, so a bifunctional diazonium salt can be used to cross-link side chain groups fairly indiscriminantly.

Bis-diazobenzidine is prepared by diazotization of benzidine dihydrochloride (33 mg) in 0.15 M HCl (10 ml) at 0° C. with sodium nitrite (25 mg) for 15 minutes. The pH is raised to 7–8 with 6 N NaOH and dilutions of this $10^{-2}$ M solution added with rapid stirring at 4° C. to 2.5 mg/ml orgotein in 0.025 M pH 7.5 phosphate.

At pH 7.5, $2\times10^{-4}$ M bis-diazobenzidine, the orgotein benzidine solution slowly turned reddish brown.

Gel filtration of the pH 7.5, $2 \times 10^{-4}$ M bis-diazobenzidine reacted mixture through a 35 cc Bio-GelA 0.5 column gives a series of protein fractions from $3 \times 10^{-4}$ M.W. up to the void volume (MW$>5 \times 10^5$). Most of the yellow color comes through at the void volume. Electrophoresis shows an increase in electrophoretic mobility and decrease in SOD activity with increasing molecular volume. The protein in the $3 \times 10^4$ MW region has a band structure (bands 1–8) like slightly modified native protein, but the higher molecular volume species are electrophoretically heterogeneous. The cross-linked product is a mixture of cross-linked orgoteins consisting of from two up to about 10 orgotein molecules joined together by bridging p,p'-aminobiphenyl groups.

At high pH (9.2) and with bis-diazobenizidine concentrations above $2 \times 10^{-4}$ M, the orgotein precipitates as a brownish precipitate. Similarly, at pH 7.5 at $5.5 \times 10^{-5}$M bis-diazobenzidine concentrations, most of the protein precipitates.

Thus, bis-diazobenzidine readily polymerizes orgotein even at low ($<3$) molar excess. However, higher excesses cause precipitation and loss of SOD activity.

Following the procedure of Example 3 but substituting another orgotein congener for the bovine orgotein, e.g., human or other cogener named in Examples 1 and 2, the coresponding congeners cross-linked with a bis-diazobenzidine residue is obtained.

EXAMPLE 4

Orgotein Cross-linked by Dimethyl Suberimidate · 2 HCl

Bovine orgotein is polymerized with dimethyl suberimidate using conditions similar to those used by Bartholeyns & Moore, Science, 186, 444–445 (1974) on ribonuclease.

The extent of the resulting polymerization, based on gel chromatography, varies from dimerization on up. Raising the protein concentration and buffer concentration raises the average extent of polymerization.

The reaction product thus is a mixture of cross-linked orgoteins consisting of from two up to about 6 orgotein molecules joined by bridging $-NH-(\overset{+}{N}H_2=)C-(CH_2)_6-C(=\overset{+}{N}H_2)-NH-$ groups, which can be separated by gel chromatography as described above.

Bovine orgotein (5.5 mg) in 9.5 ml 0.1 M pH 10 phosphate buffer is reacted with 0.5 mg dimethyl suberimidate dihydrochloride for 1 hour at room temperature. The pH is kept at 9.8 – 10.0 with 0.1 M NaoH. The reaction mixture is eluted through a 35 cc Bio-Gel A 0.5 column with 0.1 m pH 8 NH$_4$OAc to stop the reaction after 1 hour and to separate the protein according to size. Most of the protein still elutes with native orgotein, although electrophoresis shows a mixture of SOD active bands (from −4 to +3). The remainder of the protein (about ¼ of the total) elutes at higher molecular weight positions, mainly corresponding to dimer. The higher molecular weight protein is a smear in the band 1–3 position on electrophoresis.

EXAMPLE 5

Orgotein Cross-linked by Dimethyl Suberimidate · 2 HCl

In a similar manner as Example 4, 20 mg bovine orgotein is reacted with 0.5 mg. dimethyl suberimidate · 2 HCl in 0.5 ml 0.5 M Na$_2$HPO$_4$ adjusted to pH 10 with 0.1 M NaOH. After 1 hour at room temperature, the reaction is stopped by addition of 50 λ 6 N NH$_4$OAc. Gel chromatography shows there is little unpolymerized orgotein, and the orgotein polymers are primarily the trimers and tetramers as described in Example 4.

Following the procedure of Examples 4 and 5, employing the corresponding human, sheep, horse, pig, dog, rabbit, guinea pig and chicken orgotein congeners as starting protein, cross-linked products of these congeners are produced in which 5 or 6 orgotein molecules are joined together by bridging suberimidate residues. These dimeric, trimeric, tetrameric, pentameric and hexameric cross-linked products are readily speareated by gel chromatography employing Sephadex G-200.

The preceding examples can be repeated with similar success by substituting the generically or specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

What is claimed is:
1. A water-soluble, injectable cross-linked orgotein having a molecular weight of up to 500,000, wherein an orgotein molecule is intermolecularly cross-linked by at least one organic bridging group with at least one molecule of a watersoluble, injectable non-antigenic protein, said organic bridging group being formed by the reaction of orgotein or a mixture of orgotein and another water-soluble, injectable non-antigenic protein, with an organic difunctional cross-linking agent.
2. The cross-linked orgotein of claim 1 wherein the orgotein is bovine.
3. The cross-linked orgotein of claim 1 wherein the non-antigenic protein is orgotein.
4. The cross-linked orgotein of claim 3 wherein the orgotein is bovine.
5. The cross-linked orgotein of claim 3 consisting of 1 to 3 cross-linked orgotein molecules.
6. The cross-linked orgotein of claim 1 cross-linked with globulin or albumin molecules.
7. The cross-linked orgotein of claim 6 wherein the non-antigenic protein is serum albumin.
8. The cross-linked orgotein of claim 7 wherein the albumin is human serum albumin.
9. The cross-linked orgotein of claim 6 wherein the orgotein is bovine.
10. The cross-linked orgotein of claim 7 wherein an orgotein molecule is cross-linked with 1 or 2 serum albumin molecules.
11. The cross-linked orgotein of claim 8 cross-linked with one human serum albumin molecule.
12. A pharmaceutical composition having antiinflammatory activity comprising, in admixture with a pharmaceutically acceptable carrier, an antiinflammatorily effective unit dosage amount of the cross-linked orgotein of claim 1.

* * * * *